United States Patent [19]
Cox

[11] 3,989,498
[45] Nov. 2, 1976

[54] METHOD OF ODOR CONTROL

[75] Inventor: James P. Cox, Lynden, Wash.

[73] Assignee: H. Gordon Walker, Bellingham, Wash.

[22] Filed: June 23, 1975

[21] Appl. No.: 589,074

[52] U.S. Cl. .......................................... 71/3; 71/13; 71/64 SC; 210/18; 210/59; 21/55; 424/76; 260/708
[51] Int. Cl.² ...................... C05F 7/00; C05G 3/04
[58] Field of Search .................. 71/1, 3, 4, 12, 13, 71/21, 64 SC, 64 JC; 210/18, 59, 64; 21/55; 424/76; 260/708

[56] References Cited
UNITED STATES PATENTS

| | | | |
|---|---|---|---|
| 38,748 | 6/1863 | Kidwell | 71/3 |
| 51,216 | 11/1865 | Rankin | 71/3 |
| 125,886 | 4/1872 | Dutch | 71/12 |
| 2,250,345 | 7/1941 | Allison | 210/64 |
| 3,019,223 | 1/1962 | Sheers | 21/55 |
| 3,072,524 | 2/1959 | Gabelier | 21/55 |
| 3,276,186 | 10/1966 | Hronas | 210/59 |
| 3,413,218 | 11/1966 | Einsel | 210/18 |
| 3,459,852 | 8/1969 | Roehm | 210/59 |
| 3,509,254 | 4/1970 | Krotingen | 21/55 |
| 3,821,413 | 6/1974 | Hellyer | 424/76 |
| 3,883,303 | 5/1975 | Roberts | 21/55 |

FOREIGN PATENTS OR APPLICATIONS

| | | | |
|---|---|---|---|
| 1,938,634 | 2/1971 | Germany | 21/55 |
| 6,906,485 | 10/1970 | Netherlands | 210/59 |
| 142 | 1854 | United Kingdom | 71/3 |
| 3,464 | 1872 | United Kingdom | 71/3 |
| 1,396 | 1882 | United Kingdom | 71/3 |

OTHER PUBLICATIONS

Chem. Abstracts, vol. 74, 1971, 14355j, p. 70.

*Primary Examiner*—Thomas G. Wyse
*Assistant Examiner*—Ernest G. Therkorn
*Attorney, Agent, or Firm*—Robert W. Beach

[57] ABSTRACT

For the purpose of controlling odor, a slurry of digested sewage sludge to be sprayed on land for restoring its fertility is mixed with a deodorant composition containing glacial acetic acid and amyl alcohol and optionally other components including 2,3-butanedione, sulfuric acid, hydrochloric acid, benzaldehyde and copper sulfate.

6 Claims, No Drawings

METHOD OF ODOR CONTROL

BACKGROUND OF THE INVENTION

1. Field of the Invention

The present invention relates to a method of controlling the odor of digested sewage sludge slurry applied to land for restoring its fertility and to a deodorant composition suitable for use in such odor control.

2. Prior Art

In the past attempts have been made to control odors of digested sewage sludge by insuring as complete anaerobic digestion of the sludge as possible. Alternatively, or in addition to digestion in digesters, the sludge has been allowed to age in lagoons. It has not been considered feasible to utilize deodorants because of the great variety of odor-producing substances in the sludge and the great quantity of sludge to be treated.

SUMMARY OF THE INVENTION

It is a principal object of the invention to provide a deodorant composition which can be mixed with sewage sludge digested to a greater or lesser extent for the purpose of controlling odor from such sludge when it is spread as a slurry on land for restoring fertility.

A more specific object is to provide a deodorant composition containing components which will effectively counteract or mask a wide variety of disagreeable odors emanating from sewage sludge.

It is a further object to enable such deodorant composition to be utilized effectively simply by being mixed with the sewage sludge.

An additional important object is to provide a deodorant composition which will be effective over an extended period of time to control disagreeable odors emanating from the sludge.

Another object is to provide such deodorant composition which can be produced reasonably economically from materials that are rather readily available.

It is also an object to enable the formulation of the deodorant composition to be altered easily for providing the most effective odor control for different types of sludge.

The foregoing objects can be accomplished by mixing with digested sludge slurry prior to being applied to land a deodorant composition containing at least glacial acetic acid and amyl alcohol and preferably various other ingredients including sulfuric acid, 2,3-butanedione, benzaldehyde, hydrochloric acid and copper sulfate.

THE PROBLEM REQUIRING SOLUTION

For the purpose of reclaiming infertile land such as that remaining after strip mining or excessive erosion, it has been proposed to apply to the land, preferably by spraying, enriching material in the form of digested sewage sludge. Such sludge is conventionally sprayed on the land as a slurry having a concentration of 1% to 10%, and preferably between 3% and 6%, of solid material. It has been found, however, that the sludge is not completely digested, and the degree of digestion varies from one part to another of a quantity of sludge slurry. Consequently, a larger or smaller quantity of more or less disagreeable odors emanate from the sludge particularly after it has been sprayed on the land.

The problem of controlling odors emanating from sludge thus applied to land is very difficult to solve because of the large quantities of sludge used and the wide variety of odors which emanate from the sludge. It has been found that malodor constituents of representative sewage sludge are present in the following decreasing order of quantitative content: ammonia, methylamine, methane, dimethylamine, hydrogen sulfide, geosmin, trimethylamine, mucidone, ethylamine, diethylamine, triethylamine, m-propylamine, indole, isopropylamine, n-butylamine, butyric acid, skatole (metylindole), sec-butylamine, ter-butylamine, iso-butylamine, putrescene, n-methylamine, cadaverine, n-methyldiethylamine, n-amylamine, iso-amylamine. Mercaptans may or may not be present and the quantity may vary widely. These various components differ in pungency and offensiveness. The same components listed above can be rearranged as follows in descending order of obnoxiousness for the quantity of the component present, namely: geosmin, trimethylamine, mucidone, hydrogen sulfide, methylamine, dimethylamine, methane, triethylamine, ethylamine, diethylamine, m-propylamine, skatole (metylindole), indole, butyric acid, putrescene, cadaverine, n-butylamine, ter-butylamine, iso-butylamine, isopropylamine, sec-butylamine, n-methylamine, n-methyldiethylamine, n-amylamine, iso-amylamine, ammonia.

The problem, therefore, involves providing a deodorant composition including components which will either mask or counteract such malodorous substances.

SOLUTION TO THE PROBLEM

In order to control the odor of sewage sludge, a liquid deodorant composition is mixed with the sludge slurry which deodorant composition includes components which will mask or counteract the various components of the sewage sludge to a degree sufficient to eliminate or at least to reduce drastically the objectionable odor of the sludge and which will be effective for a length of time sufficient to enable the land on which the slurry is sprayed to assimilate the sludge.

The word deodorant as used herein is intended to mean a composition which eliminates, neutralizes, reodorizes, masks or counteracts offensive odors.

A desirable and effective deodorant composition for use in treating sewage sludge has the following compositions. The proportions of components are specified by weight.

Formula I

|  |  | Permissable Range |  | Preferred Proportion |
|---|---|---|---|---|
| glacial acetic acid: | $CH_3COOH$ | 2. | – 80% | 76.00% |
| amyl alcohol: | $C_5H_{11}OH$ | 1. | – 50% | 11.97% |
| 2,3-butanedione: | $CH_3COCOCH_3$ | 1. | – 50% | 9.00% |
| sulfuric acid: | $H_2SO_4$ | .01 | – 5% | 2.00% |
| benzaldehyde: | $C_7H_6O$ | .001 | – 2% | 1.00% |
| copper sulfate: | $CuSO_4$ | 0. | – 2% | .03% |
|  |  |  |  | 100.00% |

-continued

Formula II

|  |  | Permissable Range | Preferred Proportion |
|---|---|---|---|
| diluted hydrochloric acid: | HCl | 0. – 50% | 18.00% |
| water: | $H_2O$ | 1 to 5 times HCL | 18.00% |
| glacial acetic acid: | $CH_3COOH$ | 2. – 80% | 36.00% |
| amyl alcohol: | $C_5H_{11}OH$ | 1. – 50% | 13.47% |
| sulfuric acid | $H_2SO_4$ | .01 – 5% | 1.50% |
| benzaldehyde: | $C_7H_6O$ | .001 – 5% | 2.50% |
| 2,3-butanedione: | $CH_3COCOCH_3$ | 1. – 50% | 10.50% |
| Fe. ion e.g. ferric hydroxide | $Fe(OH)_3$ | 0. – 5% | .03% |
| potassium iodide | KI |  |  |
|  |  |  | 100.00% |

Optional ingredients of either formula are:

|  |  | Permissable Range |
|---|---|---|
| glucose: | $C_6H_{12}O_6$ | 0 – 50% |
| citric acid: HOOCCH$_2$C(OH)COOHCH$_2$COOH | | 0 – 20% |
| coumarin: | $C_9H_6O_2$ | 0 – 15% |

The glacial acetic acid and amyl alcohol are catalyzed by hydrogen sulfide of the sewage sludge to produce amyl acetate, an ester having the formula $CH_3COOCH_2CH_2CH(CH_3)_2$ which has a fruity odor reminiscent of bananas.

In this reaction, some hydrogen sulfide is retained by the amyl acetate and some is disassociated by the ferric hydroxide. The glucose sorbs the sulfur. The hydrogen of the hydrogen sulfide is simply liberated as nascent hydrogen. The ferric hydroxide, ferric sulfate or other soluble iron compound to produce iron ions, copper sulfate or potassium iodide serve as a catalyst to enable the glucose to sorb sulfur liberated from the hydrogen sulfide of the sewage sludge.

The proportion of glacial acetic acid exceeds that necessary to react with the amount of amyl alcohol present in the deodorant composition, and the excess glacial acetic acid neutralizes the ammonia content of the digested sludge. The resultant ammonia acetate salt has no odor.

The amyl acetate resulting from the reaction of the glacial acetic acid and the amyl alcohol reacts to some extent with the trimethylamine of the sewage sludge partially as an acid and base reaction and partially as an oxidation reaction to produce a mild fruity odor.

The 2,3-butanedione of the deodorant composition preferably is provided in a complex acid vehicle produced by synthesizing and need not be chemically pure. The 2,3-butanedione is primarily a masking agent.

The coumarin, which has an odor of new-mown hay, and the skatole and indole neutralize each other probably physically rather than chemically as a Zwaardemaker's phenomenon, so that there is no appreciable detectable odor from any of these substances. The Zwaardemaker's phenomenon is discussed in the book *Methods of Air Deodorization* by W. Summer, 1963, published by Elsevier Publishing Co., New York City, New York, at pages 52, 181 and 182.

The odor of the cadaverine is masked both by the odor of the amyl acetate resulting from the reaction of the glacial acetic acid and amyl alcohol and by the 2,3-butanedione. The action of the 2,3-butanedione may be termed a reodorizing action rather than simply a masking or counteracting action because it is believed that there is a chemical interaction between the 2,3-butanedione, the cadaverine and other malodorous components of the sewage sludge.

Citric acid is included in the deodorant composition if it is necessary to deodorize methylamine and trimethylamine. The trimethylamine produces a disagreeable odor principally when oxidized and oxidation is expedited and increased when sewage sludge slurry is atomized during spray application to land. The citric acid prevents, or at least retards, the oxidation of the trimethylamine. The oxidation deterring effect of the citric acid can be increased by including in the deodorant chemical a small amount of gallic acid, glycolic acid, butylated hydroxyanisole or butylated hydroxytoluene. The citric acid may act to bind heavy metal ions, such as copper, to inhibit such metal ions from serving as catalysts to promote oxidation of the trimethylamine. When oxidized the trimethylamine has a fishy odor.

In the example of Formula II, a portion of the glacial acetic acid has been replaced by hydrochloric acid which can be in dilute form of one part of hydrochloric acid to one to five parts of water by volume. The proportion of hydrochloric acid given in Formula II by weight refers to hydrochloric acid in undiluted form. The hydrochloric acid reaction with the amyl alcohol, like the reaction between glacial acetic acid and amyl alcohol, is catalized by hydrogen sulfide and produces an ester somewhat different from amyl acetate. Hydrochloric acid converts geosmin to argosmin which has no odor. Such acid also converts methylamine, dimethylamine, trimethylamine and mucidone to substantially odorless substances.

If methyl mercaptan is present, copper sulfate or potassium iodide will be provided to reduce it to less complex compound or compounds having little or no odor.

While the deodorant composition could be applied to land separately from the application of the sewage sludge slurry, it is preferred that the deodorant composition be mixed with the sewage sludge slurry prior to application of the slurry to the land. Normally, the digested sewage sludge is stored in lagoons until it is to be used. A bucket type dredge can then dredge the bottom of the lagoon to mix the settled material with the supernatant liquid so as to produce a substantially homogeneous slurry having a solid content of 1% to 10%, and preferably between 3% and 6%. Such slurry is then transported in tank trucks or barges to the land to be reclaimed. The proportion of deodorant composition is based on the percent of sludge solids in the slurry. If $a$ = 2 to 20 parts deodorant composition; and $b$ = percent of sludge solids (in whole numbers);

then the proposition is $a \times b$ parts of deodorant composition per million parts of slurry. An example is about 50 parts of deodorant composition to a million parts of slurry having a solid content of 3 to 6% sludge solids. The deodorant composition and the slurry will be mixed during transportation to the site of application.

At the application site, the slurry can be sprayed on the land.

When the sewage sludge is applied to the land without being treated with the deodorant composition, a variety of malodors are produced. Ammonia has a characteristic pungent odor. The amines have a fishy odor. Hydrogen sulfide has the odor of rotten eggs. Skatole has a fecal odor. Cadaverine has the odor of decaying flesh. Indole or methylmercaptan has a skunk or rotten cabbage odor. After being treated with the deodorant composition of the present invention, the digested sludge slurry has only a faint fruity odor.

I claim:

1. The method of restoring fertility to land, which comprises applying to the land a slurry of sewage sludge and deodorant composition comprising amyl alcohol and glacial acetic acid.

2. The method defined in claim 1, in which the sewage sludge is digested sludge.

3. The method defined in claim 1, in which the slurry includes from 1% to 10% digested solids.

4. The method defined in claim 1, in which the slurry includes from 3% to 6% digested solids.

5. The method defined in claim 1, in which the sludge and the deodorant composition are mixed together prior to application to land.

6. The method defined in claim 5, in which the mixed slurry is sprayed onto the land.

* * * * *